United States Patent
Turley et al.

(10) Patent No.: US 6,258,056 B1
(45) Date of Patent: Jul. 10, 2001

(54) IMPLANTER APPARATUS

(75) Inventors: Roger W. Turley, Haverhill (GB);
Mark L. Anderson, 303 S. MacKay Ave., Spring Valley, WI (US) 54767

(73) Assignee: Mark L. Anderson, Spring Valley, WI (US)

( * ) Notice: Subject to any disclaimer, the term of this patent is extended or adjusted under 35 U.S.C. 154(b) by 0 days.

(21) Appl. No.: 09/329,485

(22) Filed: Jun. 10, 1999

(51) Int. Cl.$^7$ .................................................. A61M 31/00
(52) U.S. Cl. .............................................. 604/62; 604/110
(58) Field of Search ................................ 604/61–63, 64, 604/57, 59, 110, 187, 188, 215, 236, 238, 60

(56) References Cited

U.S. PATENT DOCUMENTS

| | | | |
|---|---|---|---|
| 4,077,406 | * | 3/1978 | Sandhage et al. .................. 128/217 |
| 4,105,030 | | 8/1978 | Kercso . |
| 4,154,239 | | 5/1979 | Turley . |
| 4,400,170 | | 8/1983 | McNaughton et al. . |
| 4,447,223 | | 5/1984 | Kaye et al. . |
| 4,474,572 | | 10/1984 | McNaughton et al. . |
| 4,597,753 | | 7/1986 | Turley . |
| 4,661,103 | | 4/1987 | Harman . |
| 4,781,683 | * | 11/1988 | Wozniak et al. ....................... 604/110 |
| 4,952,206 | * | 8/1990 | Ibanez et al. ......................... 604/110 |
| 4,976,686 | | 12/1990 | Ball et al. . |
| 4,994,028 | | 2/1991 | Leonard et al. . |
| 5,279,554 | | 1/1994 | Turley . |
| 5,522,797 | * | 6/1996 | Grimm .................................. 604/61 |
| 5,672,357 | | 9/1997 | Baile et al. . |

* cited by examiner

Primary Examiner—Richard K. Seidel
Assistant Examiner—Jennifer Maynard
(74) Attorney, Agent, or Firm—Skinner and Associates

(57) ABSTRACT

An implanter comprising a housing, a hollow needle connected to the housing, a drive pin positioned within the housing and aligned with the hollow needle, and a trigger assembly operably connected to both the housing and the drive pin. The drive pin has a distal end, and further has a retracted position wherein the distal end of the drive pin is in the housing and an extended position wherein the distal end of the drive pin portion extends out of the housing. A pellet is positioned between the needle and the distal end of the drive pin when the drive pin is in the retracted position. The drive pin expels the pellet through the hollow needle when moving from the retracted position to the extended position. The trigger assembly includes a trigger that has a relaxed position and an actuated position. The drive pin moves from the retracted position to the extended position when the trigger moves from the relaxed position to the actuated position. The invention further relates to a method for implanting an object beneath a membrane, comprising the steps of: positioning an object to be implanted between a drive pin and a hollow needle; positioning a plug between the object and the drive pin; inserting the needle through the membrane; and moving the drive pin from a retracted position to an extended position to expel the object through the hollow needle and stop the needle with the plug.

5 Claims, 9 Drawing Sheets

IMPLANTER APPARATUS

BACKGROUND OF THE INVENTION

1. Field of the Invention

The present invention relates, generally, to apparatus and methods for implanting objects beneath membranes. More particularly, the invention relates to implanters for depositing electronic tracing devices, hormone pellets or other objects or pellets beneath a membrane.

2. Background Information

The state of the art in general includes various devices and methods for implanting objects beneath a membrane using a device that has a rod which travels through a hollow needle to deposit the object through the needle and beneath the punctured membrane. For example, the objects or pellets may comprise electronic tracing devices or transponders which are used to tag an animal, or the pellets may comprise hormone pellets which are used in the domestic livestock fattening industry to promote growth of the animal. The pellets are often injected into the ears of the animals to prevent the pellets from entering food products for human or animal consumption as the ears are commonly discarded in slaughtering. Typically, the ear is grabbed with one hand while the other hand operates the implanter. The pellets should be carefully, properly and accurately implanted to reduce the probability for infection and increase the effectiveness of the deposited pellets. Further, because of the movements of the animals, it is desirable for the pellets to be quickly implanted into the animal.

These devices and methods are believed to have significant limitations and shortcomings. One of the shortcomings is that implanter devices may spread blood-borne diseases among the animals if the needle is not replaced for each animal. In recognition of this problem, Turley (U.S. Pat. No. 5,279,554) disclosed a device that uses a shroud or covering that moves and locks in an extended position to partially cover the needle, and thus encourages a user to replace the needle after each use. Another shortcoming of the known art is the inability to automatically, quickly, consistently and powerfully implant multiple pellets. Turley (U.S. Pat. No. 4,154,239) disclosed that the link between the drive pin and the trigger actuator in the known art devices tended to buckle, and further disclosed that the speed or velocity of the drive pin was limited because the known art devices employed a 1:1 ratio between the drive pin and the trigger/actuator. In recognition of these problems, Turley ('231) disclosed a device that uses a flexible belt or link to achieve a velocity ratio other than 1:1. Other devices have achieved a velocity ratio other than 1:1 by attaching spur gears to the trigger and a rack gear to the drive pin.

Applicants' invention provide an implanter apparatus which is believed to constitute an improvement over existing technology.

BRIEF SUMMARY OF THE INVENTION

The present invention provides an implanter which generally comprises a housing or housing assembly, a hollow needle connected to the housing assembly through a quick attachment mechanism, a drive pin positioned within the housing assembly and aligned with the hollow needle, and a trigger assembly operably connected to both the housing assembly and the drive pin. The drive pin has a distal end, and further has a retracted position in which the distal end of the drive pin is in the housing assembly and an extended position in which the distal end of the drive pin extends out of the housing assembly. A pellet is positioned between the needle and the distal end of the drive pin when the drive pin is in the retracted position. The drive pin expels the pellet through the hollow needle as it moves from the retracted position to the extended position.

The trigger assembly includes a trigger that has a relaxed position and an actuated position. The drive pin moves from the retracted position to the extended position to expel the pellet when the trigger moves from the relaxed position to the actuated position. The trigger assembly is adapted to provide a mechanical advantage for increasing the velocity of the drive pin with respect to the velocity of the trigger. The trigger assembly includes a trigger lever having a fulcrum point, a trigger end operably contacting the trigger, and a shuttle end operably connected to a drive pin shuttle that slides along at least one shuttle guide groove to move the drive pin between the retracted position and the extended position. The fulcrum point is preferably closer to the trigger end than to the shuttle end to provide the mechanical advantage for increasing the velocity ratio between the drive pin and the trigger assembly.

The housing assembly includes a magazine housing attached to a body housing. The magazine housing has a magazine passage sized to receive a pellet magazine and contains a magazine advancement mechanism. The magazine advancement mechanism indexes the pellet magazine through a number of predetermined index positions within the magazine passage. The drive pin is adapted to extend through the pellet magazine, i.e. one of the plurality of tubes, and into the hollow needle at each one of the predetermined index positions. The magazine advancement mechanism preferably has an opening or window for viewing the index positions of the pellet magazine. The magazine advancement mechanism has at least one fixed clip for engaging one side of the pellet magazine, at least one movable clip for engaging the other side of the pellet magazine, and an index actuator for indexing the at least one movable clip within the magazine passage. The clips are adapted to prevent the pellet magazine from moving in a first direction within the magazine passage and to allow the pellet magazine to move in a second direction upon the application of an index force, which moves the movable clip in an index motion. The movable clip has a bias spring to move the movable clip from one groove, over a ridge, and to an adjacent groove upon release of an index force.

In a manual index actuator embodiment, the index force is manually applied to the index actuator to index the movable clip within the magazine passage. A bias spring provides the return motion. In an automatic index actuator embodiment, the index force is generated by an actuation force applied to the trigger. The automatic index actuator includes a cam lever pivotally attached at a fulcrum point to the housing assembly. The cam lever has a cam end in operable contact with a cam follower mounted on the drive pin shuttle. The cam lever further has a magazine advancement mechanism end in operable contact with the at least one movable clip. The magazine advancement end has an index motion and a return motion. The cam lever pivots and moves the magazine advancement end in an index motion to index the pellet magazine when the cam follower moves with the drive pin into the retracted position, and the cam lever pivots and moves the magazine advancement end in a return motion as the cam follower moves with the drive pin from the retracted position toward the extended position. A latch mechanism prevents the magazine advancement end from undergoing an index motion until the drive pin is fully retracted out of the magazine.

Each one of the tubes in the pellet magazine may include both a pellet and a plug. The pellet is positioned in front of the plug. When the drive pin extends, the pellet is expelled from the needle and the plug remains in the needle to discourage the use of the needle in another animal. The quick attachment mechanism allows the needle to be quickly replaced. Preferably, the quick attachment mechanism includes a threaded collect. The hollow needle extends through the threaded collect, and a threaded nut screws around the collect to quickly attach and detach the hollow needle from the housing assembly. The collect preferably has two or more circumferencially spaced slots that enable the collet to securely tighten around a range of needle diameters.

The features, benefits and objects of this invention will become clear to those skilled in the art by reference to the following description, claims and drawings.

DETAILED DESCRIPTION

Figure 1:
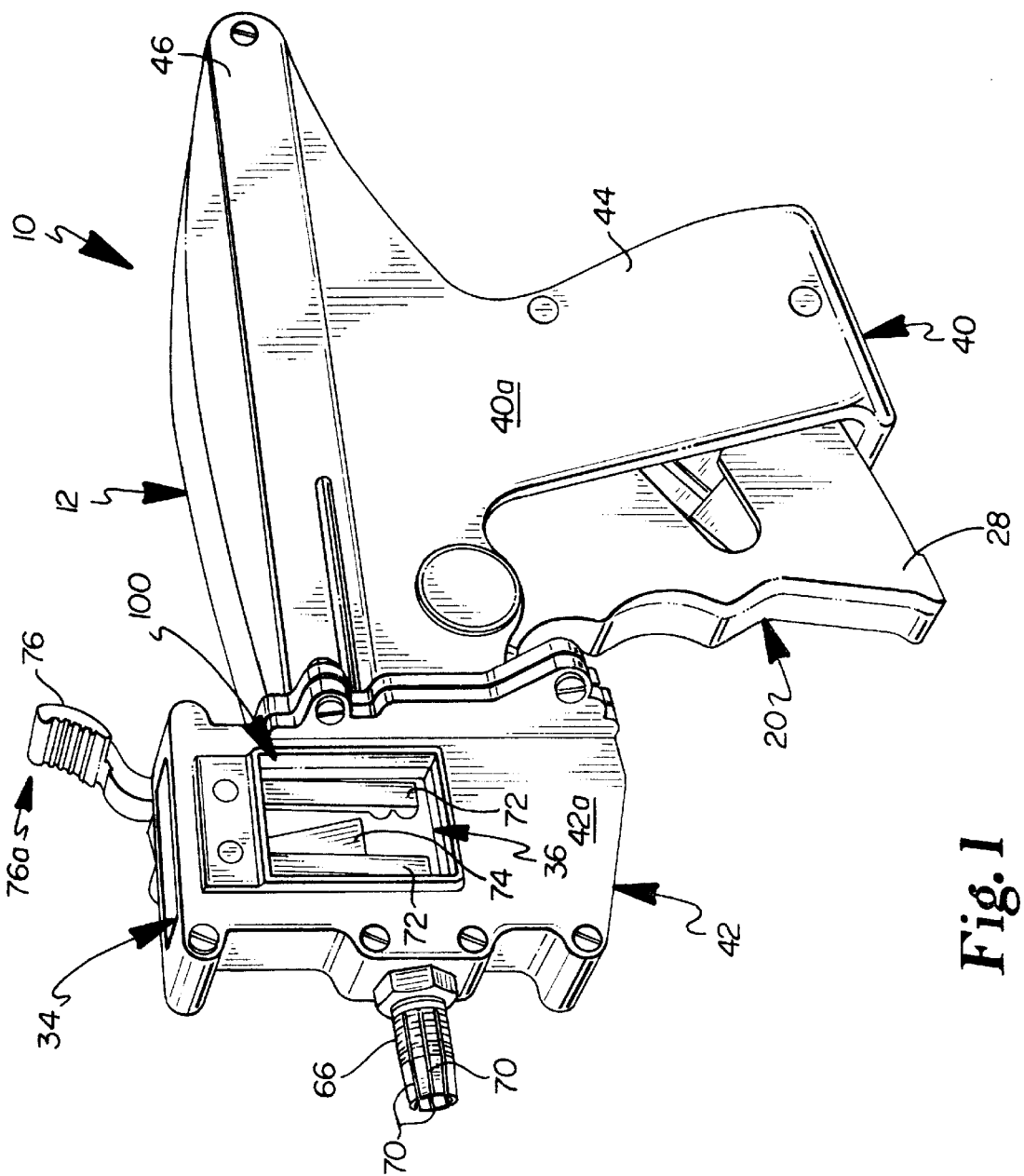
FIG. 1 is a perspective view of an embodiment of the implanter of the present invention.

FIGS. 1–16 illustrate preferred embodiments of the present invention, which is generally indicated by the reference numeral 10. The implanter 10 is described below first in terms of its major structural elements and then in terms of its secondary structural and/or functional elements which cooperate to implant an object beneath a membrane, i.e. to inject a transponder or hormone into an animal or to deposit a reactant through a stretched covering into a reaction vessel, among others.

Referring to FIGS. 1, 3, 5, 7 and 8, the implanter 10 generally comprises a housing assembly 12, a hollow needle 14 connected to the housing assembly 12, a drive pin assembly 16 including a drive pin 18 positioned within the housing assembly 12 and aligned with the hollow needle 14, and a trigger assembly 20 operably connected to both the housing assembly 12 and the drive pin 18. The drive pin 18 has a distal end 22, and further has a retracted position in which the distal end 22 of the drive pin 18 is in the housing assembly 12 and an extended position in which the distal end 22 of the drive pin 18 extends out of the housing assembly 12 and through the hollow needle 14.

Figure 5:
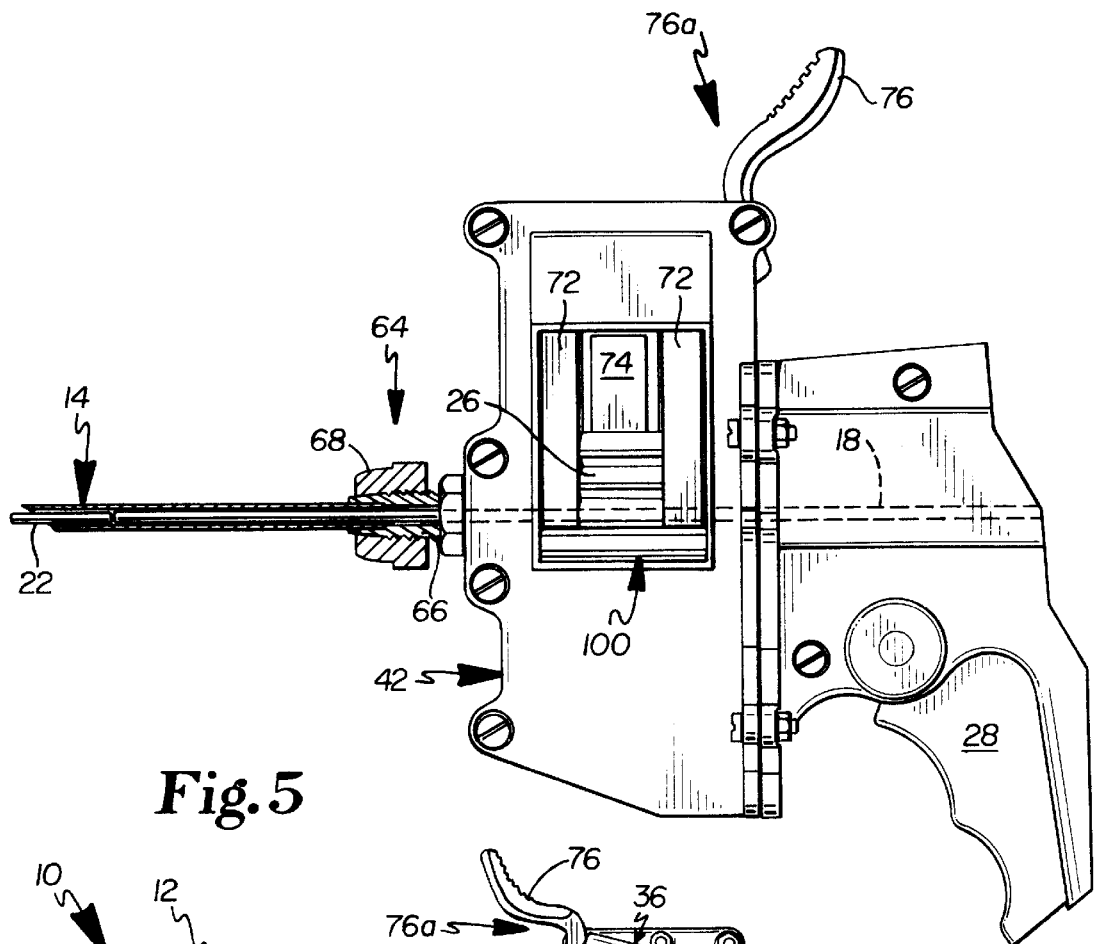
FIG. 5 is a plan view, partially in cross section, of a drive pin extending through a pellet magazine and a needle.
Figure 2:
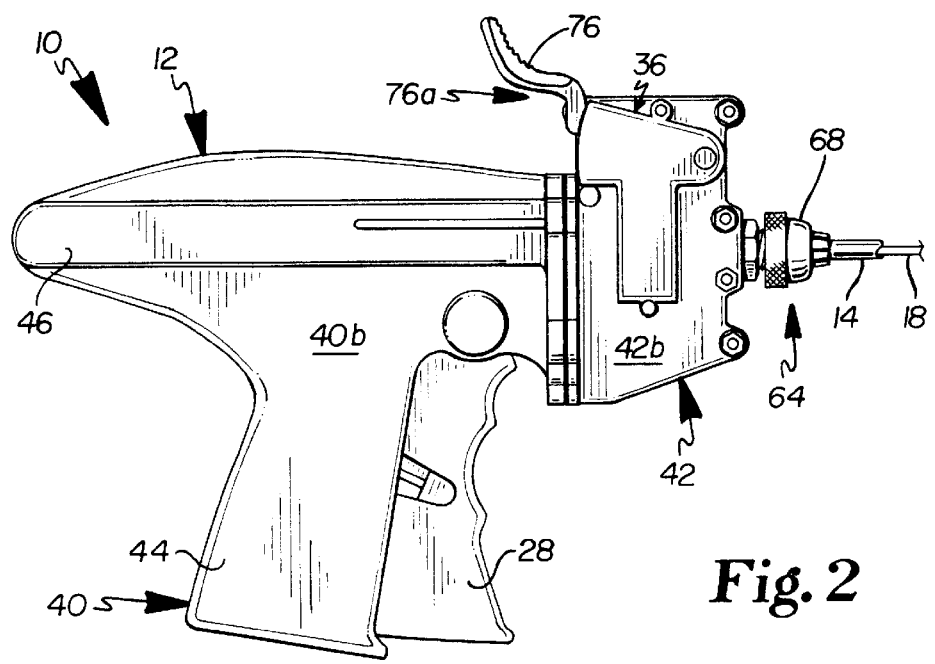
FIG. 2 is a rear plan view of the implanter of FIG. 1.
Figure 3:
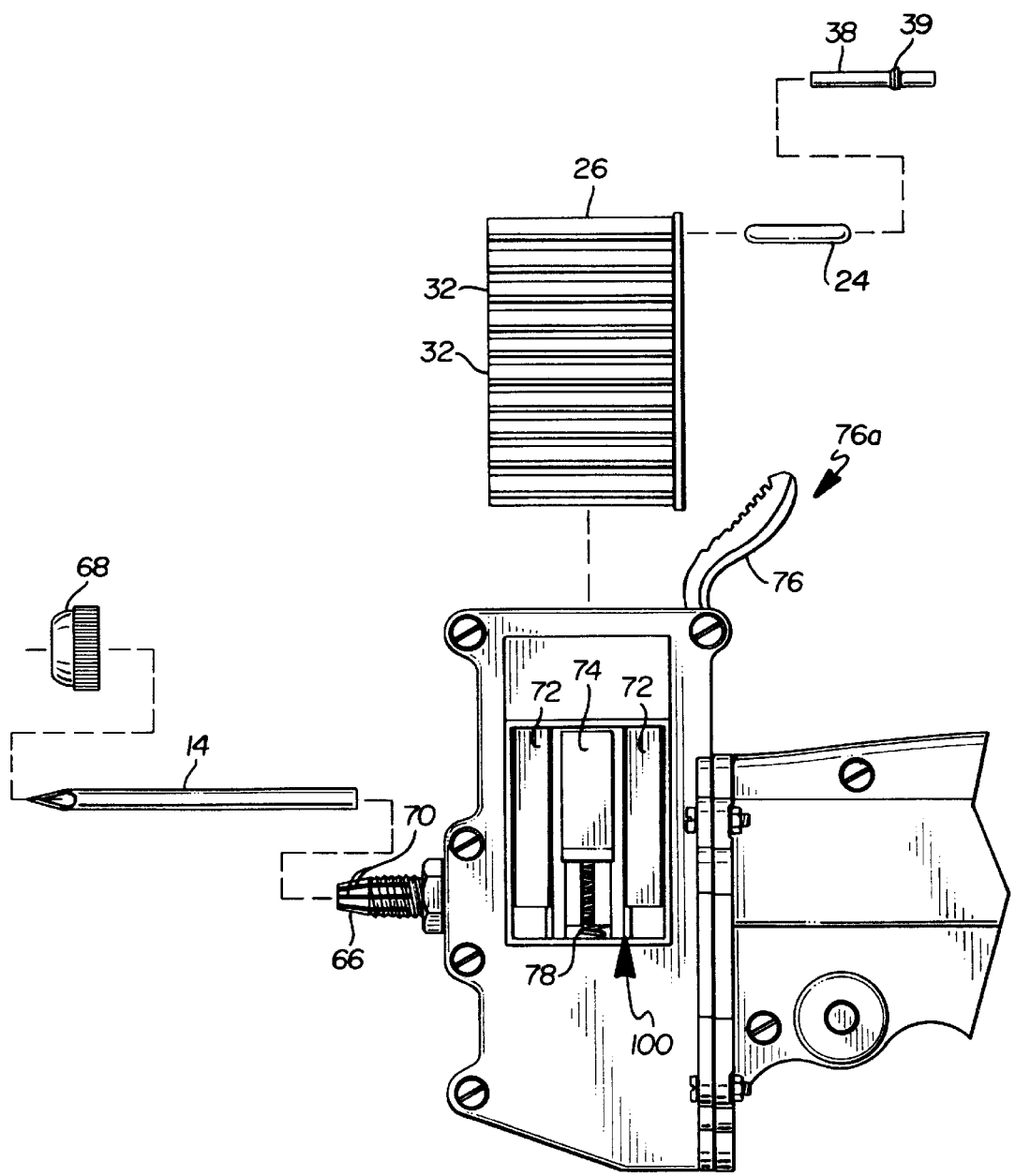
FIG. 3 is a partially exploded view of a quick attachment mechanism for a needle, a magazine housing, and of a pellet magazine having a tube loaded with both a pellet and a plug.
Figure 9:
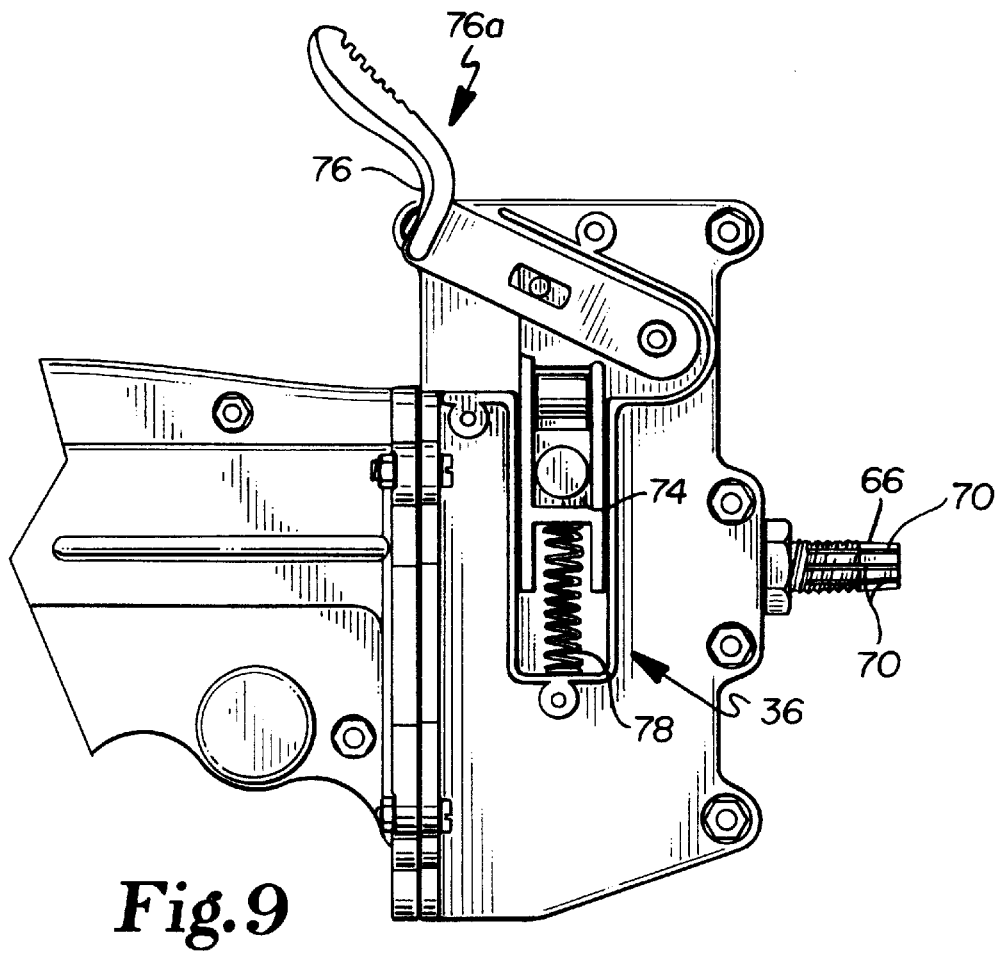
FIG. 9 is a rear view of a magazine advancement mechanism illustrating a manual index actuator.

Referring to FIGS. 3 and 5 in particular, a pellet 24 is positioned, preferably using a pellet magazine 26, between the needle 14 and the distal end 22 of the drive pin 18 when the drive pin 18 is in the retracted position. The drive pin 18 expels the pellet 24 through the hollow needle 14 as it moves from the retracted position to the extended position. The trigger assembly 20 includes a trigger 28 that has a relaxed position shown in FIG. 7, and an actuated position shown in FIG. 8. The drive pin 18 moves from the retracted position to the extended position as the trigger 28 moves from the relaxed position to the actuated position. The trigger assembly 20 is adapted to provide a mechanical advantage for increasing a drive pin velocity with respect to a trigger velocity, which provides the implanter 10 with the capability of quickly depositing an object or pellet 24. The embodiments illustrated in the figures incorporate a first class lever as a trigger lever 30 to provide the mechanical advantage that increases the drive pin velocity.

The pellet magazine 26 has a plurality of tubes 32 for holding and retaining pellets 24. The housing assembly 12 includes a magazine passage 34 sized to receive the pellet magazine 26 and contains a magazine advancement mechanism 36 for indexing the pellet magazine 26 through a number of predetermined index positions within the magazine passage 34. The drive pin 18 is adapted to extend through the pellet magazine 26 and into the hollow needle 14 when the pellet magazine 26 is at each one of the predetermined index positions. A pellet 24 may be loaded in front of a plug 38 in each one of the tubes 32 in the pellet magazine 26. The pellet 24 is positioned and adapted to be expelled from the needle 14, and the plug 38 has a shape and size to remain in the needle 14 when the drive pin 18 is extended. By remaining in the needle 14, the plug 38 discourages, and effectively prevents, the hollow needle 14 from being used again in another animal. The plug 38 may be formed from a variety of materials. In the embodiment shown in the figures, the plug 38 is a plastic object having a generally cylindrical shape. The plug 38 has a circumferencial rib 39 that causes the plug 38 to be stuck in the needle 14.

Figure 7:
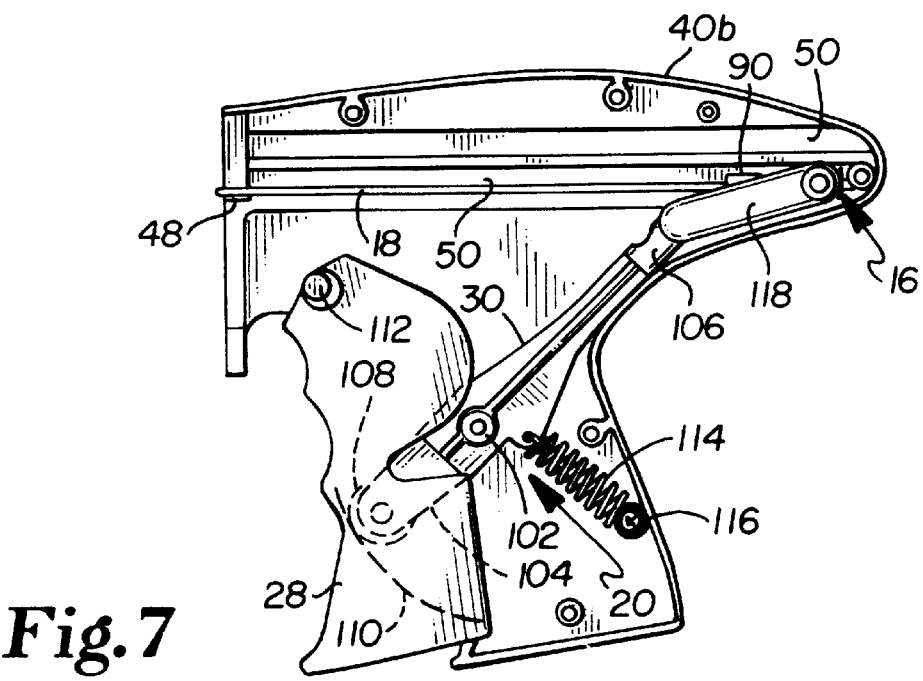
FIG. 7 is a plan view of a partially assembled housing assembly illustrating the relationship between a trigger assembly, a drive pin and a drive pin shuttle when the drive pin is in a retracted position.
Figure 8:
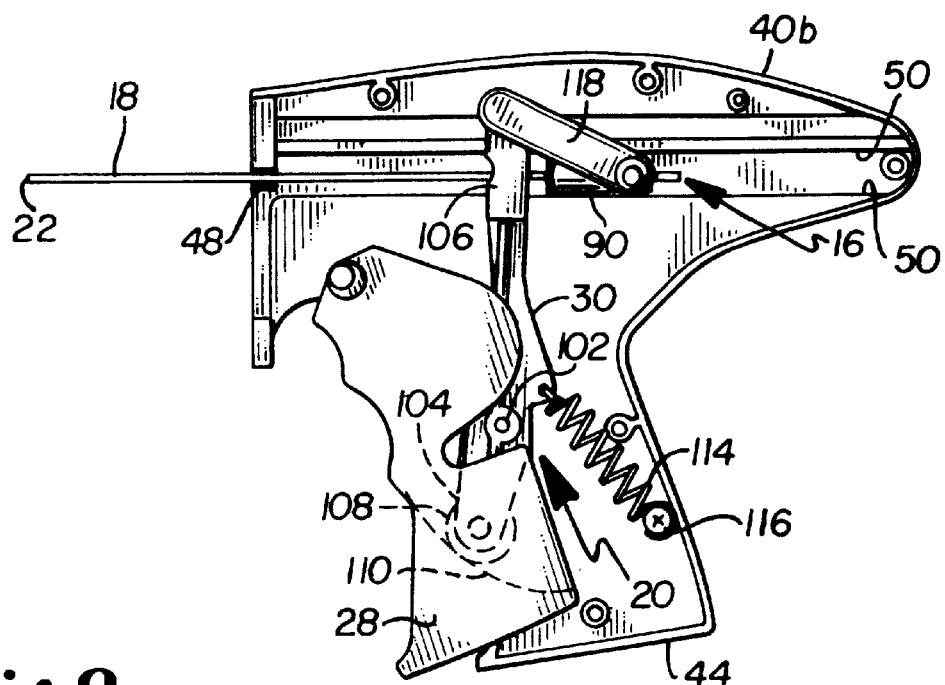
FIG. 8 is a plan view of partially assembled housing assembly illustrating the relationship between a trigger assembly, a drive pin and a drive pin shuttle when the drive pin is partially extended.

The elements of the implanter 10 are hereafter described in more detail. Many of these elements or components are constructed from molded plastic in order to provide an economical implanter 10 that is light and durable. Referring again to FIG. 1, the housing assembly 12 generally includes a body housing 40 attached to a magazine housing 42. In the embodiments shown, the body housing 40 is formed by fastening a first side 40a to a second side 40b, and the magazine housing 42 is formed by fastening together a first side 42a to a second side 42b. The body housing 40 is shaped generally like a pistol, which provides a user the ability to operate the device and accurately deposit the pellet with one hand. The body housing 40 comprises a hand grip portion 44 and a drive pin portion 46. The trigger assembly 20, and in particular the trigger 28, is positioned adjacent to the hand grip portion 44. Referring to FIGS. 7 and 8, the drive pin portion 46 is formed to include a drive pin passage 48 and a shuttle guide, which is formed by shuttle guide grooves 50 in the first and second sides 40a and 40b of the body portion 40. A drive pin shuttle 90 is connected to the proximal end of the drive pin 18, and slides along the shuttle guide. The shuttle guide and the drive pin passage 48 cooperate to accurately extend the drive pin 18 through the pellet magazine 26 and the hollow needle 14.

Figure 4:
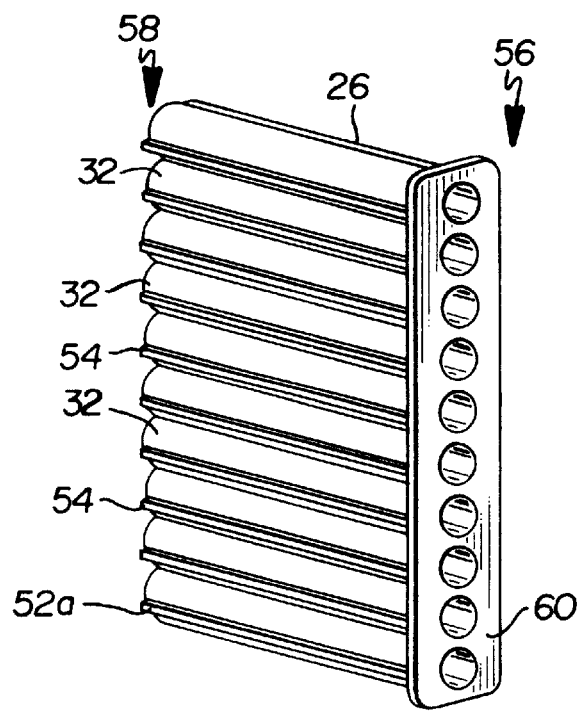
FIG. 4 is a perspective view of a pellet magazine.
Figure 13:
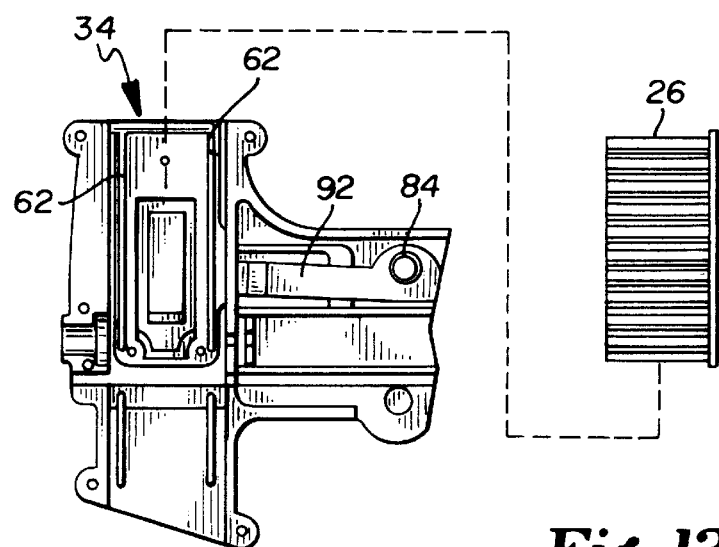
FIG. 13 is a plan view illustrating the placement of a pellet magazine within a magazine passage of a magazine advancement mechanism.

The first and second sides 42a and 42b of the magazine housing 42 form the magazine passage 34, which is sized and configured to receive the pellet magazine 26 shown in FIG. 4. The pellet magazine 26 comprises a plurality of adjacent tubes 32 formed together as a unitary body. The longitudinal axes of these tubes are parallel to each other and are generally aligned in the same plane. The pellet magazine 26 has two exterior sides 52a and 52b, each of which have a set of parallel ridges 54 and corresponding grooves. The pellet magazine 26 further has a proximal end 56 and a distal end 58. An alignment flange 60, having a generally rectangular plate-like shape, is formed at the proximal end 56 and serves as a means for properly aligning and orientating the pellet magazine 26 in the magazine passage 34. A lip having circumferencial cuts is formed around the circumference of each tube 32 at the distal end 58. The lip prevents the pellets 24 from falling out of the pellet magazine 26, but allows the drive pin 18 to easily force a pellet 24 through the lip. As illustrated in FIG. 13, the alignment flange 60 of the pellet magazine 26 corresponds to alignment grooves 62 formed in each side of the magazine housing 42 and causes the pellet magazine 26 to fit within the magazine passage 34 only in the predetermined manner.

Figure 6:
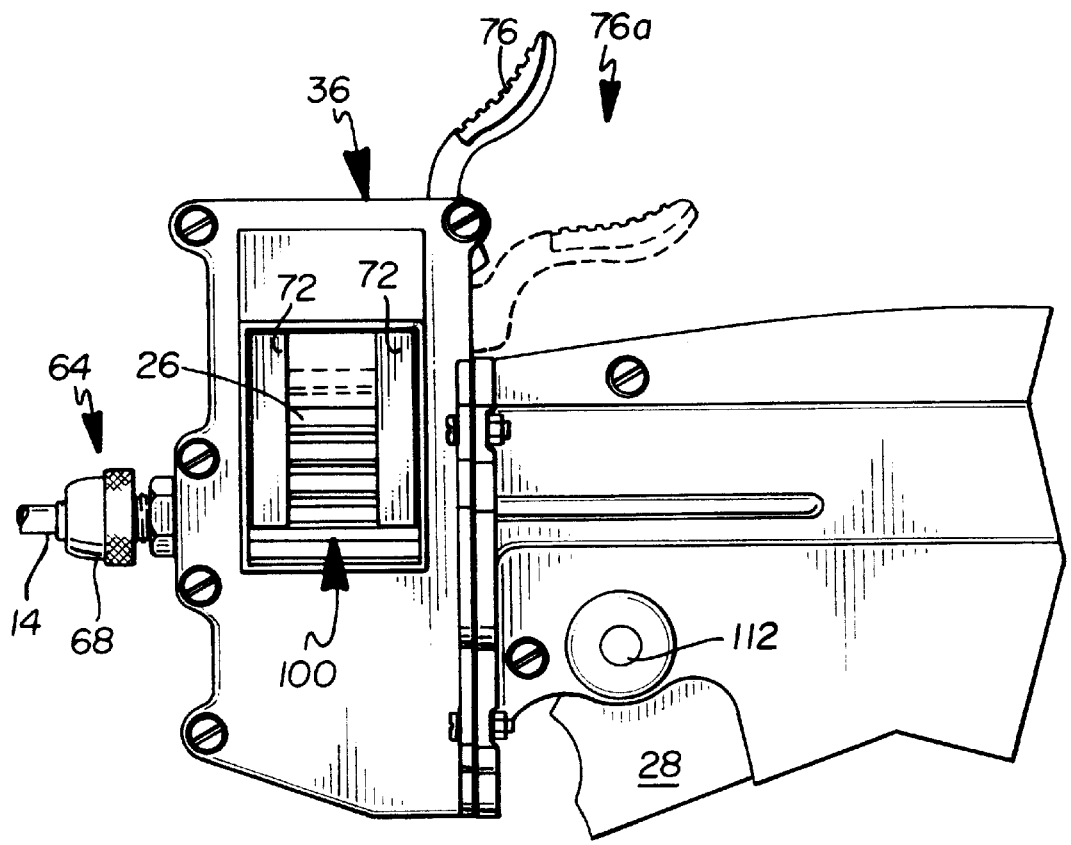
FIG. 6 is a plan view of a magazine advancement mechanism illustrating a manual index actuator.

A quick attachment mechanism 64 for a needle 14 is mounted on the distal side of the magazine housing 42. As illustrated in FIGS. 1 and 6, the quick attachment mechanism 64 preferably includes a threaded collet 66 or slotted sleeve. The hollow needle 14 extends through the threaded collet 66, and a threaded nut 68 screws around the collet 66 to quickly attach and detach the hollow needle 14 from the housing assembly 12. The collet 66 preferably has two or more circumferencially spaced slots 70 that enable the collet 66 to securely tighten around a large range of needle diameters. The collet 66 shown in the figures, for example, has six circumferencially spaced slots 70. The collet 66 is mounted to the magazine housing 42 by sandwiching the housing wall between two nuts.

Figure 10:
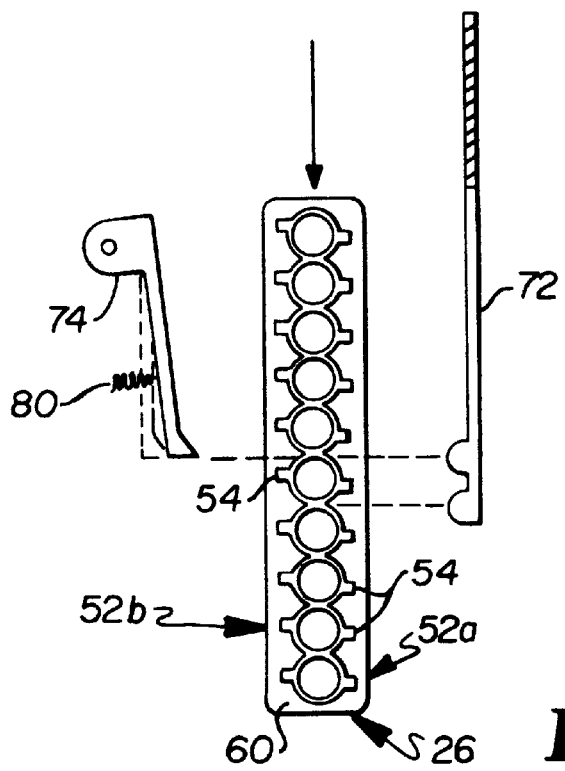
FIG. 10 is an end view illustrating the relationship between a pellet magazine and a magazine advancement mechanism.
Figure 11:
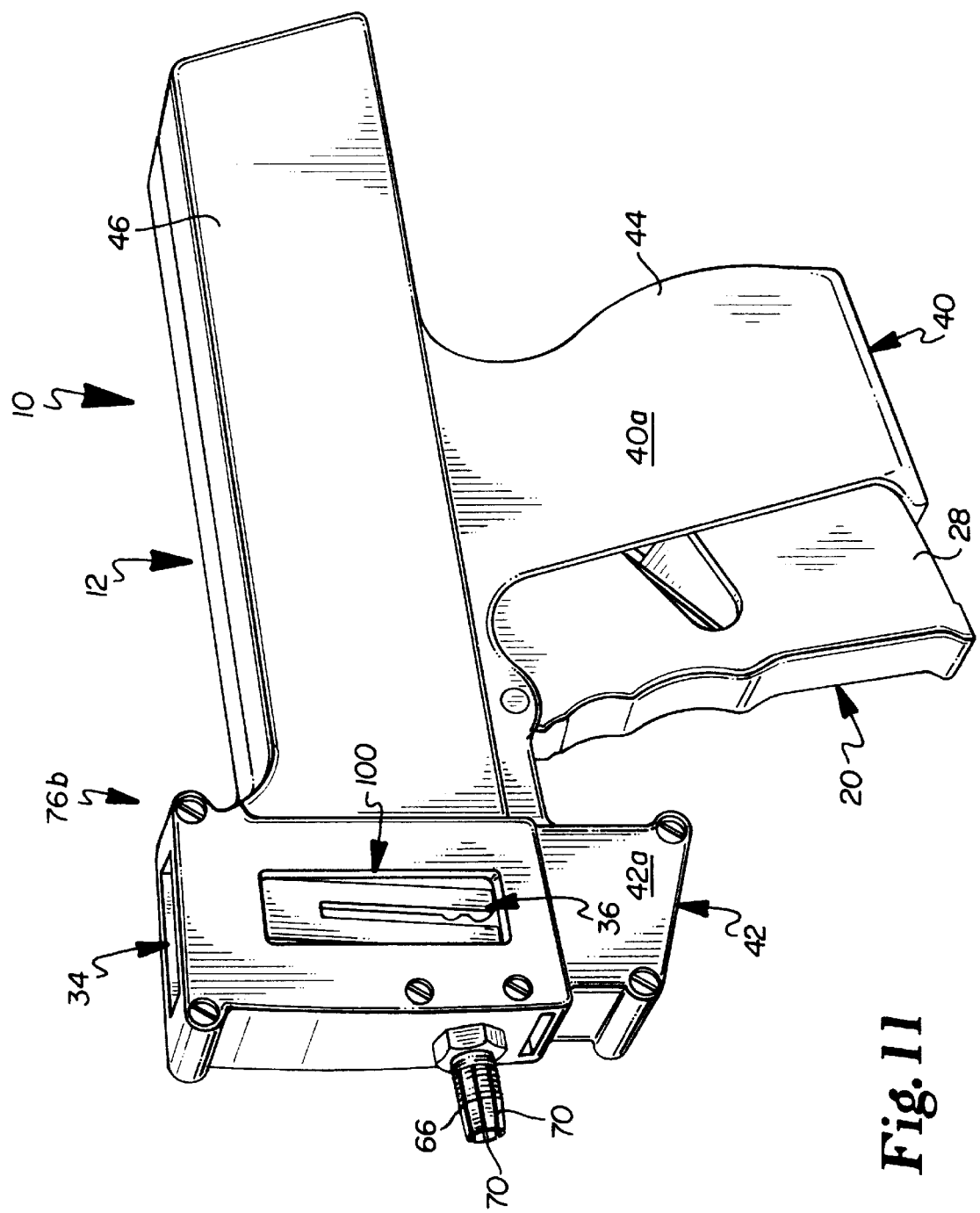
FIG. 11 is a perspective view of another embodiment of the implanter gun of the present invention.

The magazine housing 42 contains the magazine advancement mechanism 36 for indexing the pellet magazine 26. The magazine advancement mechanism 36 includes: at least one and preferably two fixed clips 72 for engaging one side of the pellet magazine; at least one and preferably one movable clip 74 for engaging the other side of the pellet magazine; and an index actuator 76 for indexing the movable clip 74 within the magazine passage 34. The clips 72 and 74 are attached to the magazine housing 42 within the magazine passage 34. As illustrated in FIG. 10, the clips 72 and 74 are adapted to prevent the pellet magazine 26 from moving in a first direction and to allow the pellet magazine 26 to move in a second direction upon the application of an index force by securely engaging the ridges 54 in the side walls of the pellet magazine 26. The movable clip 74 has a bias spring 78 and a latch spring 80 to move the movable clip 74 from one groove over a ridge 54 to another adjacent groove upon release of the index force.

Figure 12:
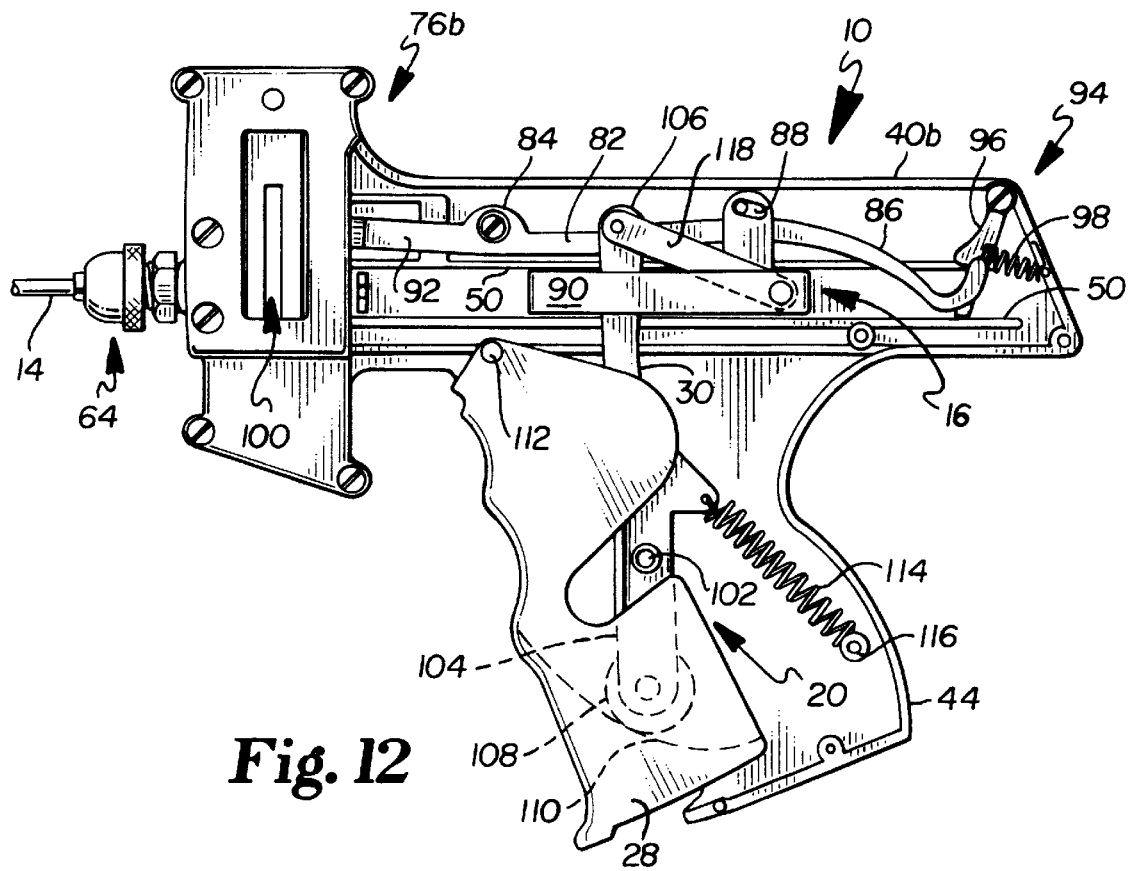
FIG. 12 is a plan view of a partially assembled housing assembly illustrating an automatic index actuator and a latched cam actuated lever.
Figure 14:
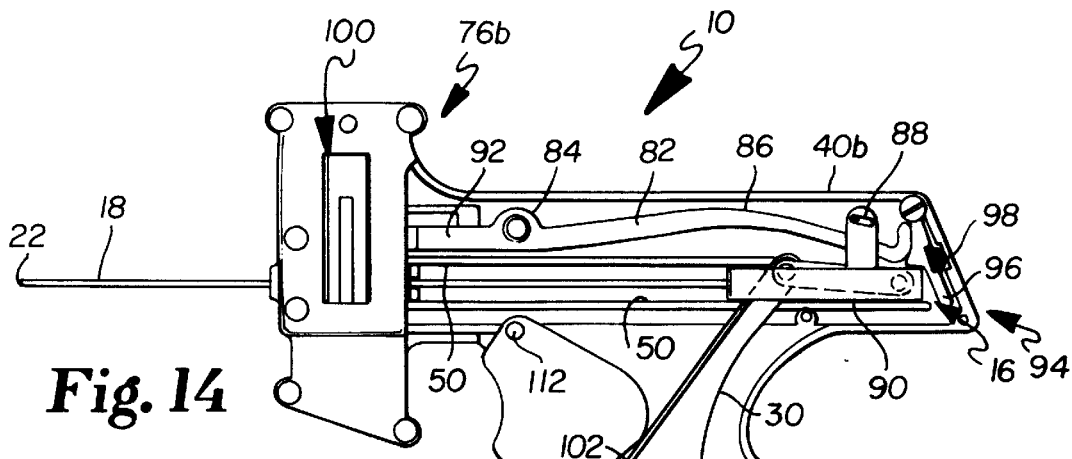
FIG. 14 is a plan view of a partially assembled housing assembly illustrating an automatic index actuator and a released cam actuated lever.
Figure 16:
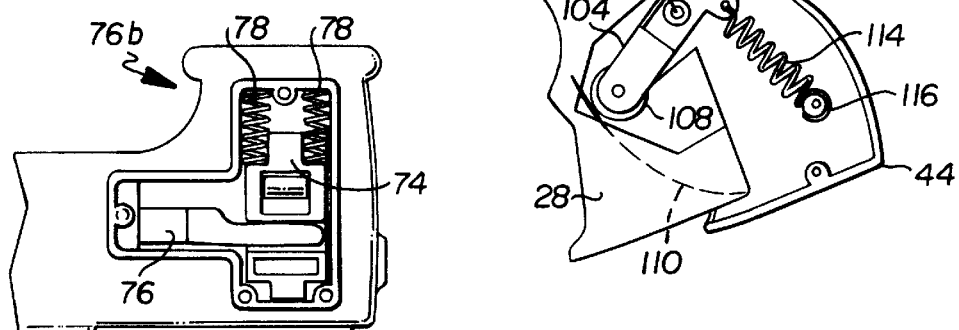
FIG. 16 is a rear plan view of the automatic index actuator of FIG. 14 and a released cam actuated lever.
Figure 15:
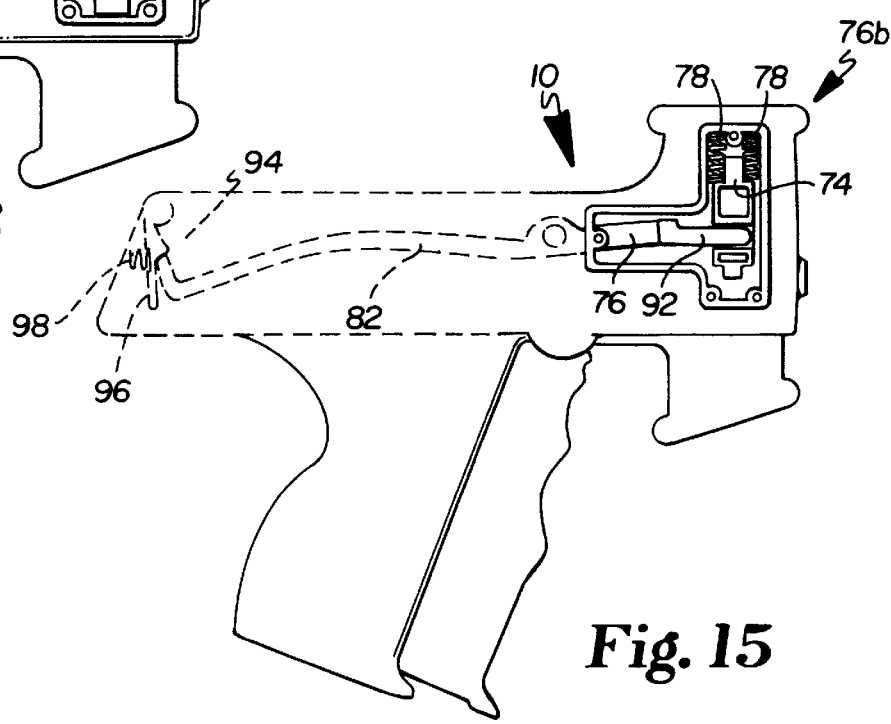
FIG. 15 is a rear plan view of the automatic index actuator of FIG. 14 and the latched cam actuated lever.

In manual index actuator embodiment 76a illustrated in FIGS. 1, 2, 6, and 9, the index force is manually applied to the index actuator 76 to index the movable clip 74 within the magazine passage 34. The bias spring 78 provides the return motion. In an automatic index actuator embodiment 76b illustrated in FIGS. 11–15, the index force is generated by an actuation force applied to the trigger 28. The automatic index actuator 76b includes a cam lever 82 pivotally attached at a fulcrum point 84 to the body housing 40b. The cam lever 82 has a cam end 86 in operable contact with a cam follower 88 mounted on a drive pin shuttle 90, which is attached to the drive pin 18. The cam lever 82 further has a magazine index end 92 in operable contact with the movable clip 74. The magazine index end 92 has an index motion and a return motion. As illustrated in FIGS. 12 and 15, the cam lever 82 pivots and moves the magazine index end 92 in a return motion as the cam follower 88 moves with the drive pin 18 from the retracted position toward the extended position. As illustrated in FIGS. 14 and 16, the cam lever 82 pivots and moves the magazine index end 92 in an index motion when the cam follower 88 moves with the drive pin shuttle 90 and drive pin 18 into the retracted position. A latch mechanism 94, comprising a latch member 96 pivotally mounted to the body housing 40 and a latch spring 98 for biasing the latch member 96 in a latch position, prevents the magazine index end 92 from undergoing an index motion until the drive pin shuttle 90 contacts the latch member 96, presses against the latch spring 98, and pushes the latch member 96 to a release position. The drive pin 18 is fully retracted out of the magazine 26 when the drive pin shuttle 90 contacts the latch member 96. The latch member 96 releases a pair of bias springs 78, shown in FIG. 16, which provide an index force to index the pellet magazine 26. The drive pin 18 is securely attached to the drive pin shuttle 90, and together form the drive pin assembly 16 that cooperates with the drive pin passage 48 and shuttle guide in the body housing 40 to consistently and accurately extend and retract the drive pin 18 along a line extending through the pellet magazine tubes 32, the collet 66, and the hollow needle 14. The index position of the pellet magazine 26 is seen through an opening or window 100 in the magazine housing 42.

The trigger assembly 20 is adapted to provide a mechanical advantage for increasing a drive pin velocity with respect to a trigger velocity, and thus allow the implanter 10 to quickly deposit the pellet. The embodiments illustrated in FIGS. 7, 8, 12 and 14 incorporate a first class lever 30, wherein the effort or actuation force is applied at the trigger 28 and the load is applied at the drive pin shuttle 90, to provide the mechanical advantage to increase the drive pin velocity. The trigger assembly 20 includes the trigger lever 30 which has a fulcrum point 102, a trigger end 104 operably contacting or connected to the trigger 28, and a shuttle end 106 operably connected, through a trigger linkage 118, to the drive pin shuttle 90 that slides along the shuttle guide grooves 50 to move the drive pin 18 between the retracted position and the extended position. The fulcrum point 102 is preferably closer to the trigger end 104 than to the shuttle end 106 to provide the mechanical advantage to increase the velocity ratio between the drive pin 18 and the trigger 28. A cam follower 108 is connected at the trigger end 104 of the trigger lever 30 and a cam surface 110 is formed in the interior of the trigger 28. The trigger 28 is attached to the body housing 40 at a pivot point 112. The trigger 28 pivots about this point 112 upon the application of an actuation force. The cam surface 110 within the trigger 28 is formed to cause the cam follower 108 and the trigger end 104 to pivot back toward the hand grip portion 44, which causes the shuttle end 106 to pivot forward to extend the drive pin 18. A trigger bias spring 114 is attached between the trigger lever 30 and a spigot 116 in the hand grip portion 44 of the body housing 40 to bias the shuttle end 106 and the drive pin shuttle 90 in the retracted position. The force of the trigger bias spring 114 is sufficient to overcome the force of the latch spring 98.

The implanter 10 described above is used to implant an object 24 beneath a membrane. The method for implanting an object 24 beneath a membrane generally comprises the steps of positioning an object 24 to be implanted between a drive pin 18 and a hollow needle 14, positioning a plug 38 between the object 24 and the drive pin 18, inserting the needle 14 through the membrane, and moving the drive pin 18 from a retracted position to an extended position to expel the object 24 through the hollow needle 14 and to stop the needle 14 with the plug 38. This method has advantages related to preventing blood borne diseases when the object is implanted in an animal. The stopped needle is replaced with an unstopped needle before implanting another object in another animal. Replacing the needles is quick and easy using the quick attachment mechanism 64, and generally requires the steps of unscrewing the nut 68 off of the threaded collet 66, removing the stopped needle from the collet 66, placing an unstopped needle in the collet 66, and screwing the nut 68 onto the collet 66. Furthermore, the steps of positioning an object 24 to be implanted between a drive pin 18 and a hollow needle 14 and positioning the plug 38 between the object 24 and the drive pin 18 is quickly and easily accomplished by pre-loading a plurality of objects 24 and plugs 38 in a magazine 26 of tubes and indexing the magazine 26 to position each object 24 and plug 38 between the drive pin 18 and the needle 14. Additionally, the step of moving the drive pin 18 from a retracted position to an extended position to expel the object 24 through the hollow needle 14 and to stop the needle 14 with the plug 38 is quickly and easily accomplished by actuating a trigger 28, and the step of indexing the magazine 26 to position each object 24 and plug 38 between the drive pin 18 and the needle 14 is quickly and easily accomplished by releasing the trigger 28.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. An implanter, comprising:
   (a) a housing;
   (b) a single use hollow needle connected to said housing;
   (c) a drive pin positioned within said housing and aligned with said hollow needle, said drive pin having a distal end, said drive pin further having a retracted position wherein said distal end of said drive pin is in said housing and an extended position wherein said distal end of said drive pin portion extends out of said housing and into said needle;
   (d) a trigger operably connected to both said housing and said drive pin, said trigger having a relaxed position and an actuated position, said drive pin moving from said retracted position to said extended position when said trigger moves from said relaxed position to said actuated position; and
   (e) a magazine attached to said housing, said pellet magazine having at least one tube containing a plug and a pellet disposed in front of said plug, said pellet being adapted to be expelled through said needle by said drive pin extending through said tube and into said hollow needle, said plug remaining in said needle to discourage said needle from being used.

2. The implanter of claim 1, further including a quick attachment mechanism attached to said housing, said quick attachment mechanism being adapted to quickly connect and disconnect said hollow needle.

3. The implanter of claim 2, wherein said quick attachment mechanism includes a threaded collet and a threaded nut that screws around said threaded collet to fasten said hollow needle to said housing.

4. An implanter for depositing an object beneath a membrane, comprising:
   (a) a housing assembly having a shuttle guide, said housing assembly including a magazine housing attached to a body housing, said magazine housing having a quick attachment mechanism, said magazine housing having a magazine passage sized to receive a pellet magazine, said pellet magazine having at least one tube for retaining a dry pellet and a needle blocking plug disposed behind said pellet, said plug having a unitary, cylindrical configuration with a circumferential rib for engaging a needle, said magazine housing containing a magazine advancement mechanism for indexing said pellet magazine through a number of predetermined index positions within said magazine passage;
   (b) a single use hollow needle connected to said magazine housing through said quick attachment mechanism, said quick attachment mechanism including a threaded collet and a threaded nut which screws around said threaded collet to fasten said single use needle for quickly connecting and disconnecting said hollow needle from said magazine housing;
   (c) a drive pin assembly positioned within said housing assembly, said drive pin assembly including a drive pin aligned with said hollow needle and a drive pin shuttle attached to said drive pin, said drive pin having a distal end, said drive pin further having a retracted position wherein said distal end of said drive pin is in said housing assembly and an extended position wherein said distal end of said drive pin portion extends out of said housing assembly and into said hollow needle, wherein said pellet and said plug are positioned between said needle and said distal end of said drive pin when said drive pin is in said retracted position and said drive pin expels said pellet through said hollow needle when moving from said retracted position to said extended position, said plug remaining in said needle to prevent additional pellet expulsion and to discourage said needle from being used again, said drive pin shuttle sliding along said shuttle guide as said drive pin moves between said retracted position and said extended position; and (d) a trigger assembly operably connected to both said housing assembly and said drive pin shuttle, said trigger assembly including a trigger that has a relaxed position and an actuated position, said drive pin moving from said retracted position to said extended position when said trigger moves from said relaxed position to said actuated position.

5. A method for implanting an object beneath a membrane, comprising the steps of:

(a) positioning an object to be implanted between a drive pin and a single use hollow needle;

(b) positioning a plug between the object and the drive pin;

(c) inserting the needle through the membrane; and (d) moving the drive pin from a retracted position to an extended position within the needle to expel the object through and out of the hollow needle and to move the plug into the needle to stop the needle with the plug; and (e) replacing the stopped needle after implanting the object into a membrane with an unstopped needle before implanting the object into a second membrane by unscrewing a nut off of a threaded collet, removing the stopped needle from the collet, placing the unstopped needle in the collet, and screwing on the nut onto the collet.

* * * * *